(12) United States Patent
Ho et al.

(10) Patent No.: US 10,888,385 B2
(45) Date of Patent: Jan. 12, 2021

(54) CALIBRATION DEVICE AND CALIBRATION METHOD FOR SURGICAL INSTRUMENT

(71) Applicant: POINT ROBOTICS MEDTECH INC., Hsinchu (TW)

(72) Inventors: Ming-Chun Ho, Hsinchu (TW); Che-Wei Su, Hsinchu (TW); Shyue-Cherng Juang, Hsinchu (TW)

(73) Assignee: POINT ROBOTICS MEDTECH INC., Hsinchu (TW)

( * ) Notice: Subject to any disclaimer, the term of this patent is extended or adjusted under 35 U.S.C. 154(b) by 398 days.

(21) Appl. No.: 16/029,678

(22) Filed: Jul. 9, 2018

(65) Prior Publication Data

US 2020/0008889 A1 Jan. 9, 2020

(51) Int. Cl.
*A61B 90/00* (2016.01)
*A61B 17/16* (2006.01)
(Continued)

(52) U.S. Cl.
CPC .......... *A61B 34/30* (2016.02); *A61B 17/1671* (2013.01); *A61B 17/34* (2013.01); *B25J 9/1692* (2013.01); *A61B 2560/0228* (2013.01)

(58) Field of Classification Search
CPC .. A61B 17/1622–1624; A61B 17/1757; A61B 17/34; A61B 2017/00725;
(Continued)

(56) References Cited

U.S. PATENT DOCUMENTS 5,987,960 A 11/1999 Messner et al.
7,213,598 B2 5/2007 Zeiss et al.
(Continued)

FOREIGN PATENT DOCUMENTS

CN 203530705 U 4/2014
CN 107361859 A 11/2017

OTHER PUBLICATIONS

Ulrich Karras: "Festo Didactic 8046573 de", Oct. 1, 2016 (Oct. 1, 2016); p. 7.

*Primary Examiner* — Dale Moyer
(74) *Attorney, Agent, or Firm* — ScienBiziP, P.C.

(57) ABSTRACT

A calibration device for a computer-assisted surgical instrument includes a rigid body, stabilization members, and references structurally or mechanically complementary to the stabilization members and disposed on opposite sides of a manipulator of the instrument. Kinematic state of the manipulator is defaulted when the calibration device is connected to the instrument by the stabilization members passing through the rigid body and removably attaching to the references. A calibration method for a computer-assisted surgical instrument implemented by a computer system includes the steps of: prompting a user to connect the calibration device to the instrument; determining if the calibration device is properly connected to the instrument; and generating default kinematic information of the manipulator of the instrument if the calibration device is properly connected to the instrument. The calibration device and method effectively improve accuracy and precision of computer-assisted surgeries.

14 Claims, 13 Drawing Sheets

(51) Int. Cl.
*A61B 34/30* (2016.01)
*B25J 9/16* (2006.01)
*A61B 17/34* (2006.01)

(58) Field of Classification Search
CPC .... A61B 2018/00988; A61B 2034/105; A61B 2034/107; A61B 2034/2055; A61B 2090/3937; A61B 2090/3983; A61B 2560/0223; A61B 2560/0228; A61B 2560/0233; A61B 34/30; A61G 17/1671; B25J 9/1692
See application file for complete search history.

(56) References Cited

U.S. PATENT DOCUMENTS

| | | |
|---|---|---|
| 8,442,677 B2 | 5/2013 | Shoham |
| 2004/0054489 A1 | 3/2004 | Moctezuma De La Barrera et al. |
| 2007/0270685 A1* | 11/2007 | Kang ..................... A61B 90/03 600/424 |
| 2008/0071272 A1 | 3/2008 | Shoham et al. |
| 2011/0015650 A1* | 1/2011 | Choi ...................... A61B 34/30 606/130 |
| 2011/0054449 A1* | 3/2011 | Tien ....................... A61B 34/20 606/1 |
| 2011/0113852 A1* | 5/2011 | Prisco .................... G01B 11/18 73/1.15 |
| 2012/0143084 A1 | 6/2012 | Shoham |
| 2013/0123580 A1 | 5/2013 | Peters et al. |
| 2018/0049795 A1* | 2/2018 | Swayze .......... A61B 17/320092 |
| 2020/0016758 A1* | 1/2020 | Keller ................... A61B 34/30 |

* cited by examiner

CALIBRATION DEVICE AND CALIBRATION METHOD FOR SURGICAL INSTRUMENT

FIELD

The present disclosure relates to a calibration device and method, and more particularly to a device and method for calibrating the kinematic state of computer assisted surgical instruments that enhances accuracy and precision of computer-assisted surgeries.

BACKGROUND

Numerous surgical operations require high manual precision on the part of the surgeon. For example, surgical orthopedic operations require the surgeon to mill, drill or saw a bone of a subject at a precise location and at a precise angle in order to fit a given implant into the bone or to shape the bone to create a desired geometric profile. Such operations are usually performed by free-hand, with the surgeon holding a specific surgical instrument and following a trajectory based on anatomical landmarks. Accuracy of the surgical operations is thus dependent on the skill of the surgeon in following the predetermined surgical plan with the hand-held surgical instrument.

Taking the advantages of information technology and robotics, computer assisted surgery has offered a reliable option in improving the accuracy and precision of surgical operations. Computer assisted surgery utilizes a tracking system to correlate the location of an anatomical site with location of the operating tool of the surgical instrument so as to enable dynamic referencing of the anatomical site with the operating tool intra-operatively on the navigation system. For example, Shoham discloses in U.S. patent publication No. 20120143084 a tracking system that includes a trackable marker mounted on the surgical site and another marker mounted on a gripping body of the instrument and/or on a robotically controlled platform connected to a moveable operating tool of the instrument, to allow tracking of the orientation of the operating tool real-time during surgical operations.

However, in addition to tracking the orientation of the operating tool, tracking the position of the tip of the operating tool during surgical operations is also critical in assessing the compliance of the current surgical status (e.g., depth of tool entry at the surgical site) with the predetermined surgical plan. Existing challenges of tracking the position of the tip of the movable operating tool as provided by Shoham lies in that it is impossible to mount a trackable marker on the tool tip during surgery and that, without mounting a trackable marker on the tool tip, it is difficult to determine the precise position of the tip of the movable operating tool.

BRIEF SUMMARY OF THE DISCLOSURE

An objective of the present disclosure is to provide a calibration device and method for calibrating the kinematic state of a robotically controlled manipulator of a surgical instrument.

Another objective of the present disclosure is to provide a calibration device and method for defining the default kinematic state of the robotically controlled manipulator of the surgical instrument, therefore allowing tracking of the tip of the surgical tool on the instrument during computer assisted surgeries.

An embodiment of the present disclosure provides a calibration device for a computer-assisted surgical instrument. The calibration device includes a rigid body, a plurality of stabilization members, and a plurality of references structurally or mechanically complementary to the stabilization members and disposed on opposite sides of a manipulator of the instrument. Kinematic state of the manipulator is defaulted when the calibration device is connected to the instrument by the stabilization members passing through the rigid body and removably attaching to the references.

Preferably, the calibration device further includes a connection sensing mechanism for detecting a state of connection between the calibration device and the instrument. The connection sensing mechanism includes at least one transmitter-receiver pair or one marker-reader pair disposed on the calibration device and the instrument respectively.

Preferably, a spatial sensor system associated with the instrument is calibrated when the calibration device is connected to the instrument.

Preferably, manipulator sensors of the instrument is calibrated when the calibration device is connected to the instrument.

Preferably, default kinematic information generated from the defaulted kinematic state of the manipulator is utilized as a calculation basis for determining a position of a tip of a tool of the instrument according to control signals generated by a computer system associated with the instrument for altering the kinematic state of the manipulator.

Preferably, the rigid body of the calibration device is formed as a part of an instrument holder, and the instrument holder includes a structure that fits at least a portion of the instrument.

Another embodiment of the present disclosure provides a calibration method for the computer-assisted surgical instrument and implemented by a computer system. The calibration method includes the steps of: (S1) prompting a user to connect the calibration device to the instrument; (S2) determining if the calibration device is properly connected to the instrument; and (S3) generating default kinematic information of the manipulator of the instrument if the calibration device is properly connected to the instrument, or returning to Step S1 if the calibration device is not properly connected to the instrument.

Preferably, the calibration method further includes a step of: adjusting the manipulator so that the kinematic state of the manipulator is close to the defaulted kinematic state.

Preferably, the calibration method further includes a step of: prompting the user to adjust the manipulator so that the kinematic state of the manipulator is close to the defaulted kinematic state.

Preferably connection between the calibration device and the instrument is determined according to receipt of a confirmation signal entered by the user.

Preferably, connection between the calibration device and the instrument is determined according to receipt of a confirmation signal sent from the connection sensing mechanism.

Preferably, the step of generating default kinematic information of the manipulator further includes a step of: calibrating a spatial sensor system associated with the instrument according to the default kinematic information.

Preferably, the step of generating default kinematic information of the manipulator further includes a step of: calibrating the manipulator sensors of the instrument according to the default kinematic information.

Preferably, the default kinematic information is utilized as a calculation basis for determining a position of a tip of a tool of the instrument according to control signals generated by the computer system for altering the kinematic state of the manipulator.

In sum, the various embodiments of the present disclosure provide an easy-to-operate calibration device for calibrating the kinematic state of the robotically controlled manipulator of computer assisted surgical instruments and for defining the default kinematic state of the manipulator so as to enable the computer system to track the tip of the surgical tool when the user is operating the instrument. The calibration device and method effectively improve the accuracy and precision of computer-assisted surgeries.

BRIEF DESCRIPTION OF THE DRAWINGS

The accompanying drawings illustrate one or more embodiments of the present disclosure and, together with the written description, explain the principles of the present disclosure. Wherever possible, the same reference numbers are used throughout the drawings to refer to the same or like elements of an embodiment.

In accordance with common practice, the various described features are not drawn to scale and are drawn to emphasize features relevant to the present disclosure. Like reference characters denote like elements throughout the figures and text.

DETAILED DESCRIPTION OF THE PREFERRED EMBODIMENTS

Figure 1:
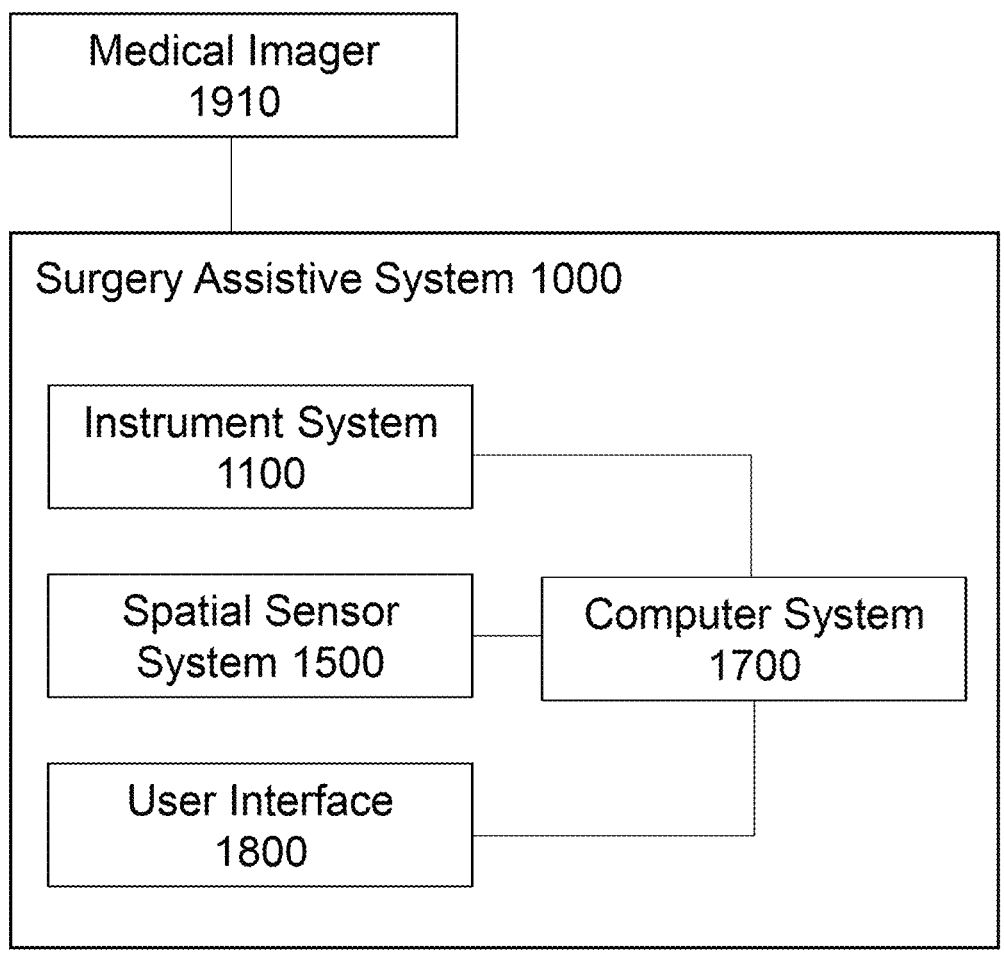
FIG. 1 is a block diagram of a surgery assistive system in accordance with an embodiment of the present disclosure.

The present disclosure will now be described more fully hereinafter with reference to the accompanying drawings illustrating various exemplary embodiments of the disclosure. The present disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the terms "and/or" and "at least one" include any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present disclosure.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 2:
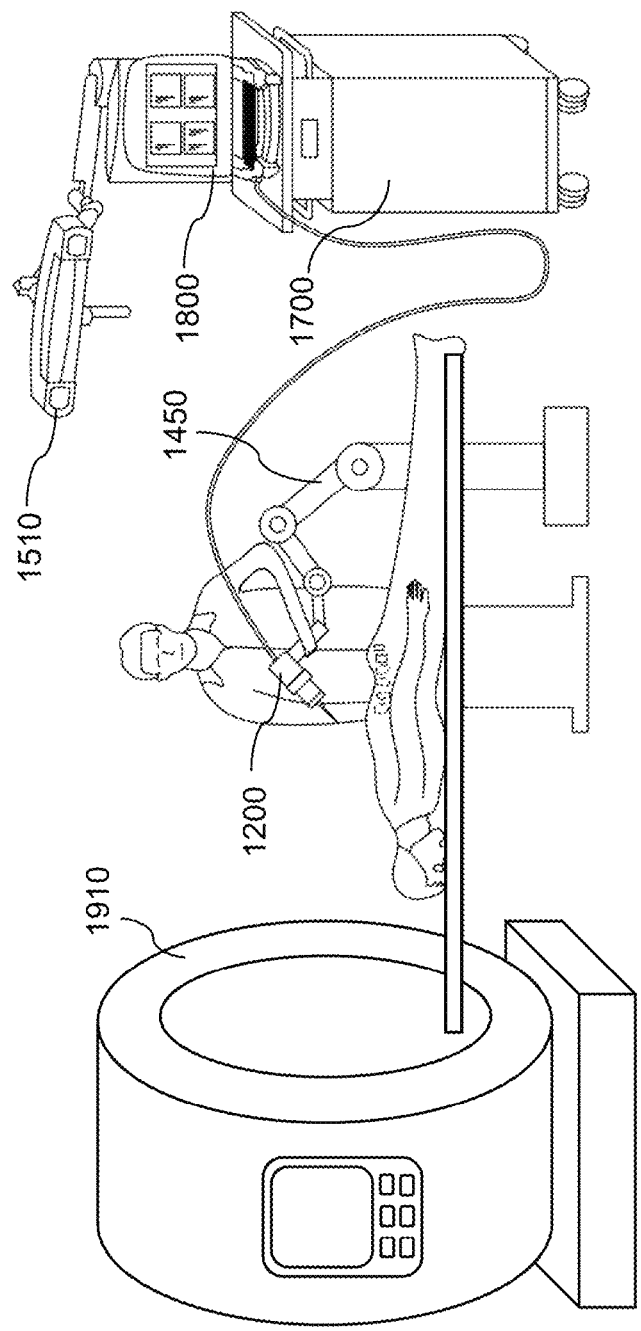
FIG. 2 is a schematic illustration of the surgery assistive system in accordance with an embodiment of the present disclosure.

Referring now to FIG. 1 and FIG. 2. According to an embodiment of the present disclosure, a surgery assistive system 1000 for pre-surgical and surgical operations includes surgical hardware coupled with electronic modules and processor-executable instructions. The surgery assistive system 1000 includes an instrument system 1100, a spatial sensor system 1500, a user interface 1800, and a computer system 1700 electrically connected to the instrument system 1100, the spatial sensor system 1500, and the user interface 1800. In the embodiment, the surgery assistive system 1000 allows a user (e.g., a surgeon) to conduct surgery on a subject (e.g., a patient) by the instrument system 1100 with reference to the user interface 1800. At least one medical imager 1910 is in communication with the surgery assistive system 1000 and is configured to acquire medical images of the subject and transmit the images to the surgery assistive system 1000. The spatial sensor system 1500 is configured to generate spatial information of the subject and the environment. The computer system 1700 is configured to generate a virtual anatomical model according to the medical images and a surgical plan according to the virtual anatomical model, to track the surgical environment according to the spatial information received from the spatial sensor system 1500, and to control movement or alter the kinematic state of the manipulator 1210. The user interface 1800 visualizes the anatomical model and allows the user to navigate through the operating field according to the surgical plan.

As illustrated in FIG. 2, the instrument system 1100 of the surgery assistive system 1000 includes a hand-held instrument 1200 for performing surgery on the subject. In the embodiment, the instrument system 1100 may further include a support arm 1450 connected to the instrument 1200 to reduce weight load on the hands of the user and optionally provide more operational stability during surgeries.

Figure 3:
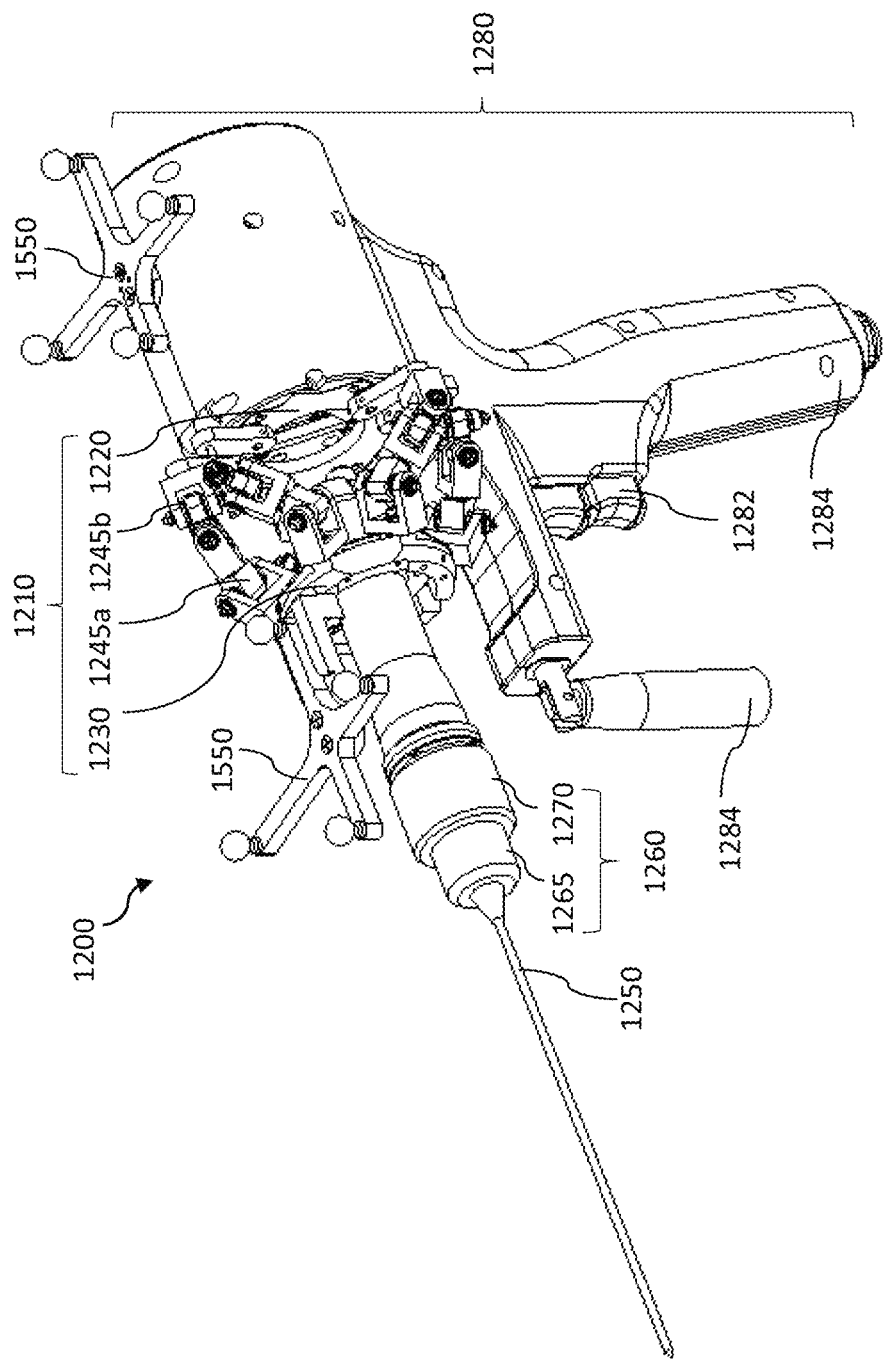
FIG. 3 is a perspective view of a hand-held instrument of the surgery assistive system in accordance with an embodiment of the present disclosure.
Figure 4:
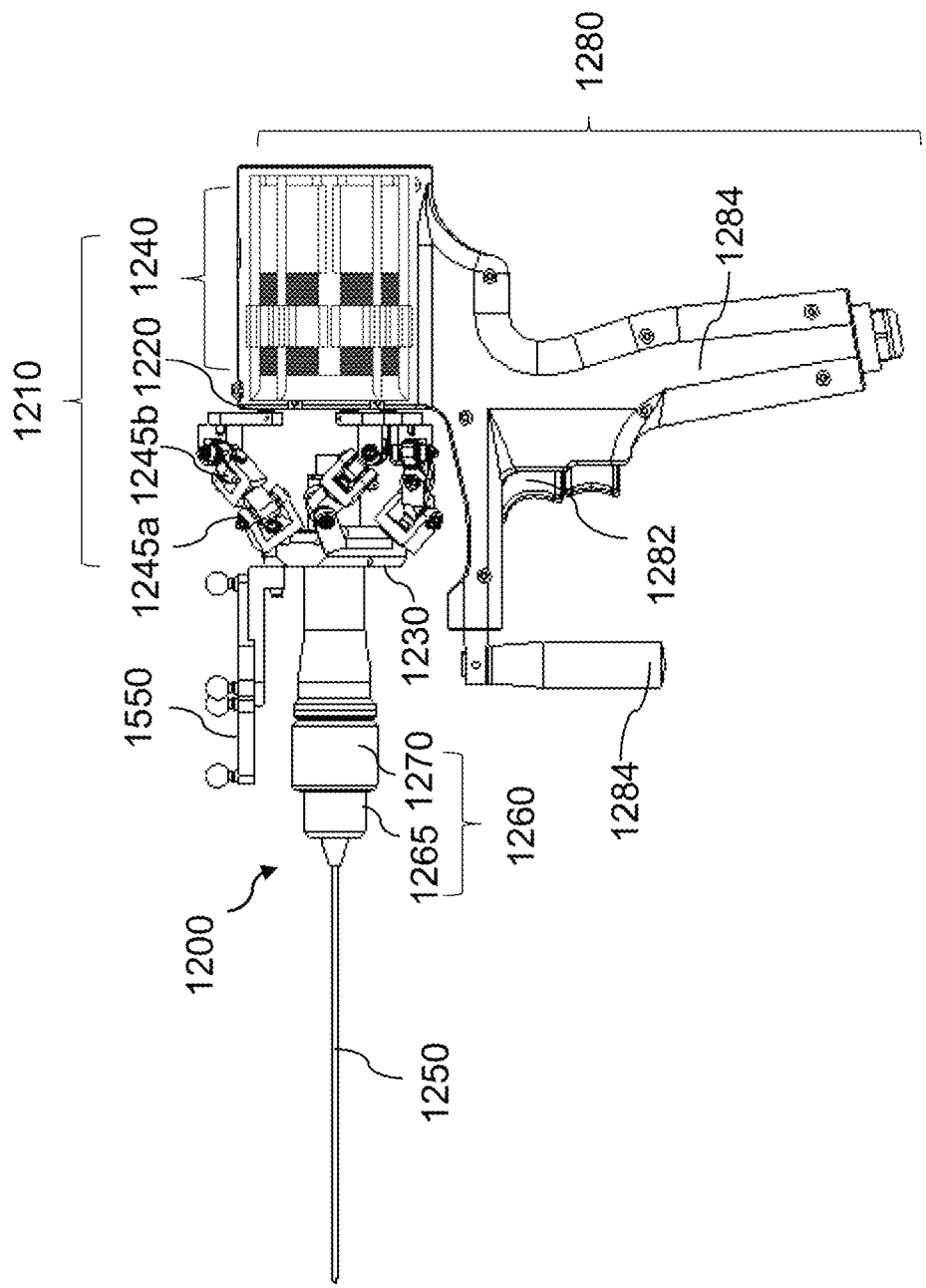
FIG. 4 is a side view of the hand-held instrument of the surgery assistive system in accordance with an embodiment of the present disclosure.

Referring to FIG. 3 and FIG. 4. According to an embodiment, the hand-held instrument 1200 includes a tool 1250, a tool installation base 1260, a manipulator 1210, and an instrument housing 1280. The tool 1250 is configured to contact or modify an anatomical surface on a body part of the subject. The tool installation base 1260 is connected to an end of the tool 1250 and the manipulator 1210 so that the tool 1250 is stably connected to the manipulator 1210. The manipulator 1210 is a mechanism controlled by the computer system 1700 for manipulating the position and orientation of the tool 1250. The instrument housing 1280 is connected to the manipulator 1210 to accommodate at least a portion of the manipulator 1210 and provide one or more handles 1284 for allowing the user to hold onto and maneuver the instrument 1200 during operation of the surgery assistive system.

In the embodiment, the tool 1250 may be a probe or indicator for contacting or assessing an anatomical site of the subject and detecting the structure or status of the anatomical site. The tool 1250 may be a drill bit, bur, curette, saw, screwdriver or other tool commonly used in surgical medicine that modifies or removes a portion of the tissues at the anatomical site by drilling, milling, cutting or scraping. In some embodiments, the tool 1250 is a mechanical, optical or ultrasound probe for performing surface matching registration and may be, but is not limited to, a rigid probe, a pressure sensor, a piezoelectric sensor, an elastomeric sensor, an optical camera, a laser scanner or an ultrasonic scanner.

Figure 5:
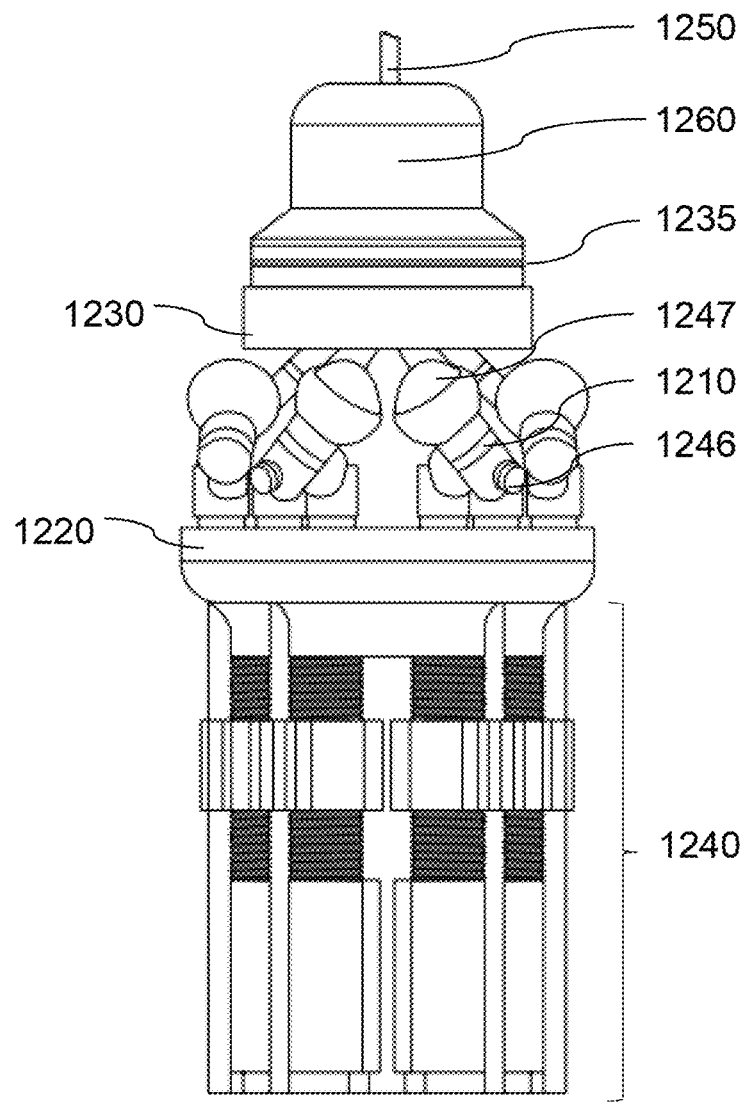
FIG. 5 is a side view of a manipulator of the hand-held instrument of the surgery assistive system in accordance with an embodiment of the present disclosure.
Figure 6:
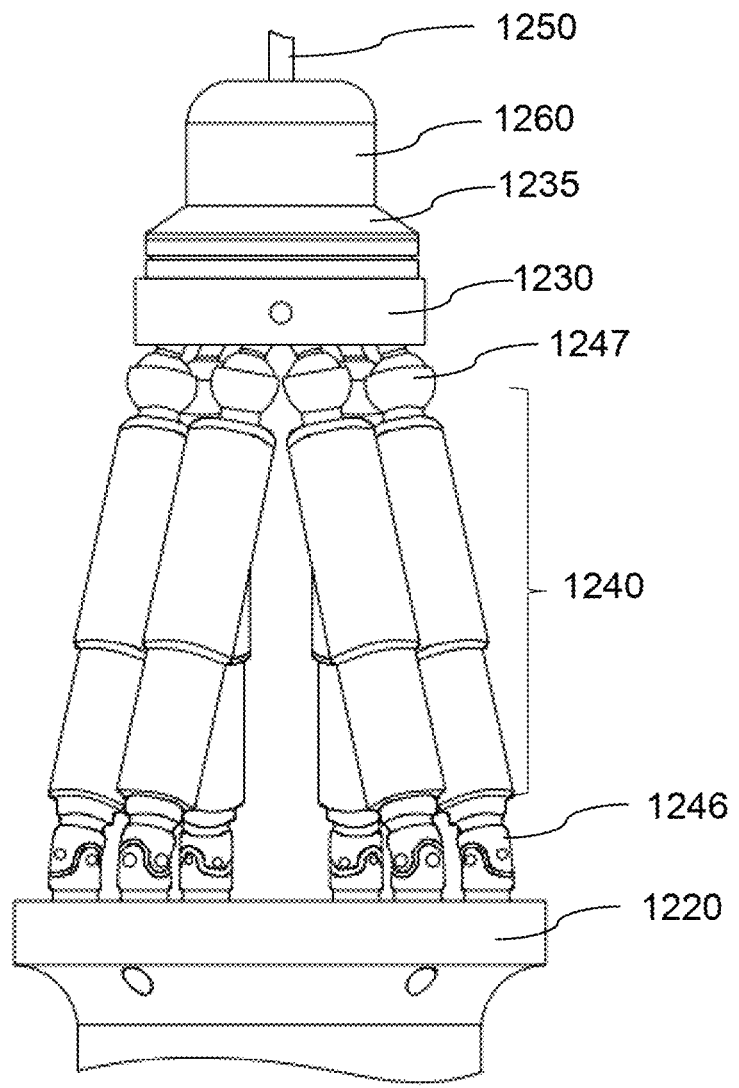
FIG. 6 is a side view of another manipulator of the hand-held instrument of the surgery assistive system in accordance with an embodiment of the present disclosure.

In the embodiment, the tool installation base 1260 is connected to the tool 1250 and a first side of a robotically controlled platform 1230 of the manipulator 1210. The tool installation base 1260 includes a tool adaptor 1265 and a motor 1270 connected to the tool adaptor 1265. The tool adaptor 1265 may be a clamp or other fastening structure for holding an end of the tool 1250 firmly to avoid displacement of the tool during operations. The motor 1270 may be a direct current (DC) motor or an alternating current (AC) motor for transducing electric energy into mechanical energy and generating a linear or rotary force to drive movement of the tool 1250. In an alternative embodiment, the motor may be disposed at the rear end of the instrument to reduce loading on the manipulator 1210 during operation of the instrument and to redistribute the weight of the instrument 1200 for improved user ergonomics. Additionally, as illustrated in FIG. 5 and FIG. 6, the tool installation base 1260 may further include a force sensor 1235 connected to the first side of the platform 1230 for detecting the force and/or torque sustained by the tool 1250 during surgeries. In other embodiments, the force sensor 1235 may be disposed in the probe or tool of the instrument; alternatively, the instrument 1200 may further include another force sensor (not shown in figures) disposed in the probe or tool. The force sensor may be, but is not limited to, a strain gauge, a force-sensitive resistor, a pressure transducer, a piezoelectric sensor, an electroactive polymer or an optical fiber bending sensor.

In the embodiment, the manipulator 1210 includes a base 1220, the platform 1230 connected to the tool installation base 1260, a plurality of joints 1245a, 1245b mounted on a second side of the platform 1230 away from the tool 1250 and on a first side of the base 1220 facing the platform 1230, and a plurality of actuators 1240 connected to the base 1220 on a second side of the base 1220 away from the platform 1230. As illustrated in FIG. 4, the base 1220 may be immobilized on or accommodated in the instrument housing 1280. The manipulator 1210 may be a parallel manipulator, such as a Stewart manipulator with six degrees of freedom (DOFs), for higher space efficiency and maneuverability. Additionally, the manipulator is preferably made of stainless steel or carbon fiber and arranged in a specific mechanical structure that allows the manipulator 1210 to possess sufficient sustainability against the force and/or torque generated from the tool 1250 contacting the subject during surgeries.

In the embodiment, the joints of the manipulator 1210 may be, but are not limited to, revolute joints, prismatic joints, spherical joints, universal joints, cylinder joint, or any combination thereof that enables a desired DOF. As exemplified in FIG. 5 and FIG. 6, the manipulator 1210 having a general Stewart platform with six DOFs may include universal joints 1246 and spherical joints 1247 to enable broad ranges of motion and various kinematic states of the manipulator 1210. The manipulator 1210 may further include a plurality of connectors, each being connected to one of the joints 1245a and one of the joints 1245b, to enable a broader range of movement of the tool 1250. In other embodiments, the instrument 1200 may further include one or more manipulator sensors, such as angle sensors (not shown in figure) for detecting the rotational angle of the joints relative to the base 1220.

In the embodiment, the actuators 1240 of the manipulator 1210 connected to the base 1220 on the side opposite to the joints are configured to drive the joints, and the connectors if any, to move according to control signals transmitted from the computer system 1700. In an alternative embodiment, the actuators 1240 and the joints may be disposed on the same side of the base 1220. As exemplified in FIG. 6, the actuators 1240 are disposed between the base 1220 and the platform 1230, with each of the actuators 1240 being joined by a universal joint 1246 and a spherical joint 1247. The plurality of actuators 1240 may be linear actuators for higher precision and stronger sustainability. In some embodiments, the manipulator sensors of the instrument 1200 may further include one or more displacement sensors (not shown in figure) for detecting the length of each of the actuators 1240.

Referring again to FIG. 3 and FIG. 4. In the embodiment, in addition to accommodating the manipulator 1210 and providing handles, the instrument housing 1280 may further include a control module 1282 for allowing the user to trigger, halt, or adjust actions of the tool 1250 or perform other functions of the instrument 1200.

In the embodiment, the hand-held instrument 1200 may be used with a calibration device 1300 configured to calibrate kinematic state of the manipulator 1210 in respect of the instrument housing 1280 so as to ensure geometric accuracy of the instrument 1200.

Figure 7:
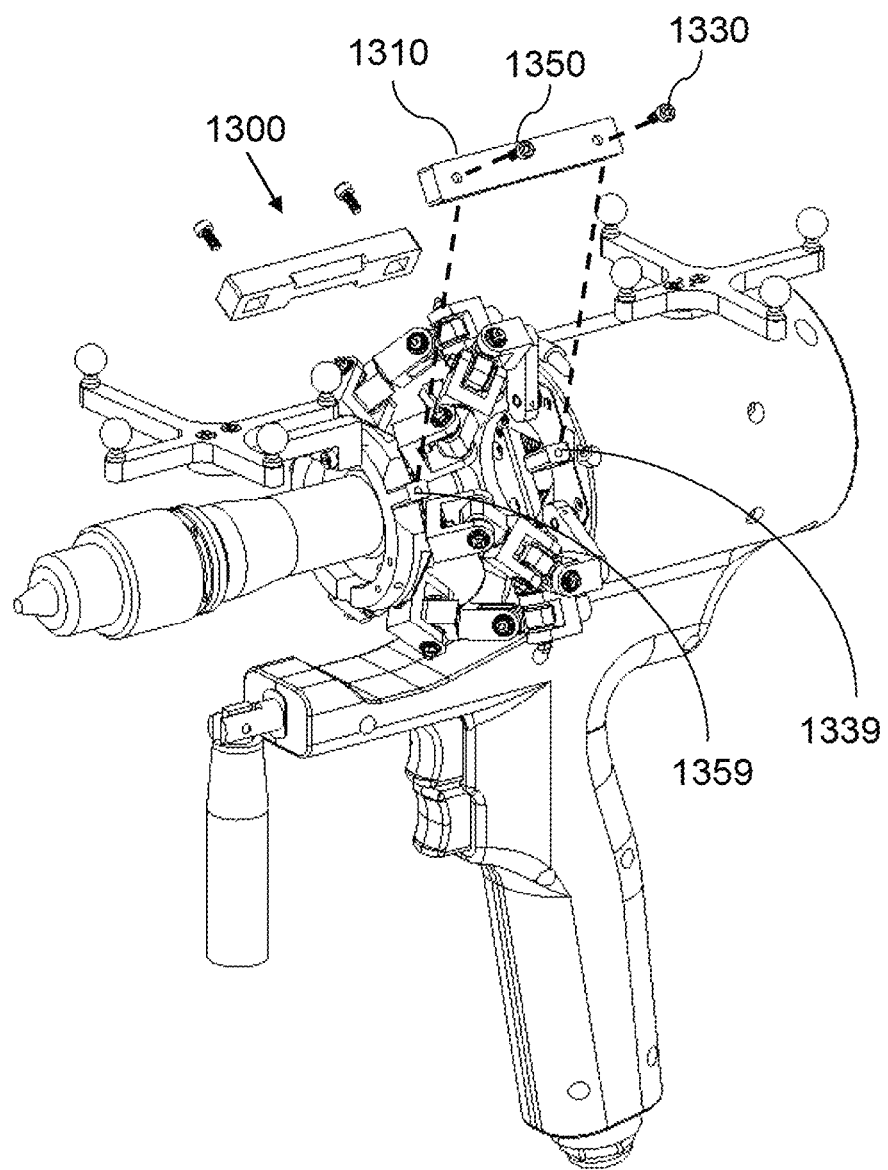
FIG. 7 is a perspective view of a calibration device for the hand-held of the surgery assistive system in accordance with an embodiment of the present disclosure.

Referring to FIG. 7. In the embodiment, the instrument 1200 may be used with a calibration device 1300 configured to calibrate the kinematic state and define a default kinematic state of the manipulator 1210 of the instrument 1200 so as to ensure geometric accuracy of the instrument 1200 and enable tracking of the tip of the tool 1250 during surgical operations. As illustrated in FIG. 7, the calibration device 1300 may include a rigid body 1310, a plurality of stabilization members 1330, 1350, and a plurality of references disposed on opposite sides of the manipulator 1210 of the instrument 1200. For example, the references may include a base-side reference 1339 disposed on the base 1220 or the instrument housing 1280, and a platform-side reference 1359 disposed on the platform 1230 or the tool installation base 1260. The stabilization members 1330, 1350 and the base-side and platform-side references 1339, 1359 may be bolts, pins, indentations, buckles, hook and loop fasteners, magnets or adhesives that are structurally or mechanically complementary to each other. Kinematic state of the manipulator 1210 is defaulted when the calibration device 1300 is connected to the instrument 1200 by the stabilization members 1330, 1350 passing through the rigid body 1310 and removably attaching to the references 1339, 1359. In other words, when connected to the instrument 1200, the rigid body 1310 constrains movement of the platform 1230 of the manipulator 1210 so that the platform 1230 is spaced apart from the base 1220 of the manipulator 1210 for a distance at a default orientation.

In another embodiment, the calibration device 1300 may further include a connection sensing mechanism for detecting the state of connection between the calibration device 1300 and the instrument 1200. The connection sensing mechanism may include, but is not limited to, at least one transmitter-receiver pair or marker-reader pair respectively disposed on the calibration device 1300 and the instrument 1200. For example, each of the transmitter-receiver pairs may include an radiofrequency identification (RFID) label and an RFID reader disposed on the calibration device 1300 and the instrument 1200 respectively, so that the RFID reader detects the RFID label when the calibration device 1300 is properly connected to the instrument 1200. Likewise, each of the marker-reader pairs may include an optical marker and a camera configured to recognize the optical marker.

Figure 8:
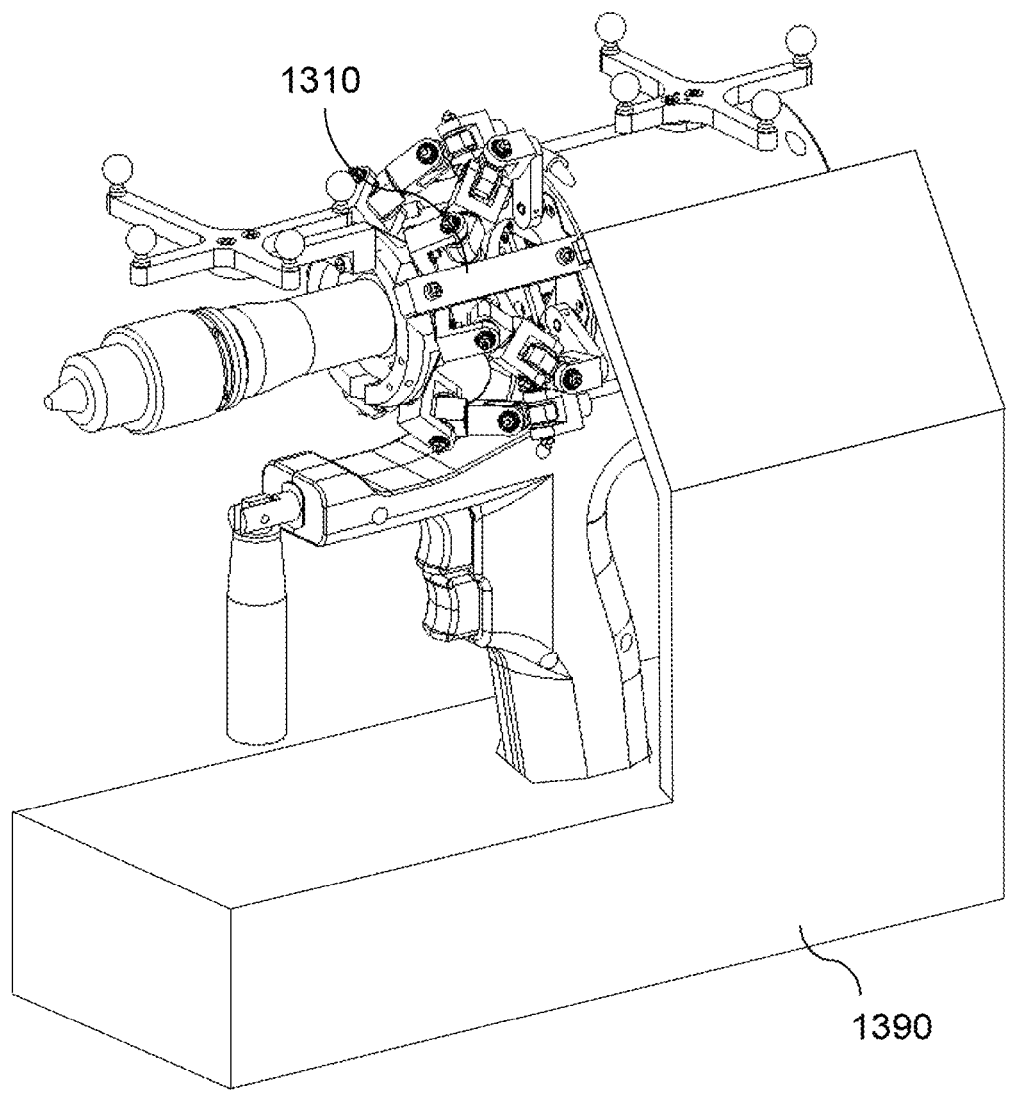
FIG. 8 is a perspective view of another calibration device for the hand-held of the surgery assistive system in accordance with an embodiment of the present disclosure

Referring to FIG. 8. In an embodiment of the present disclosure, the rigid body 1310 may be formed as a part of an instrument holder 1390 that can stand on a surface or be connected to an object in the surgical environment. The instrument holder 1390 may also include a structure that fits at least a portion of the instrument 1200 so as to allow the instrument 1200 to stand or rest on the instrument holder 1390 when not in use. In another embodiment, the calibration device 1300 may further include a container structure (not shown in figure) for accommodating the manipulator 1210 or the actuators 1240 to provide stabilization and protection for the manipulator 1210 or the actuators 1240 during transportation and storage.

Figure 9:
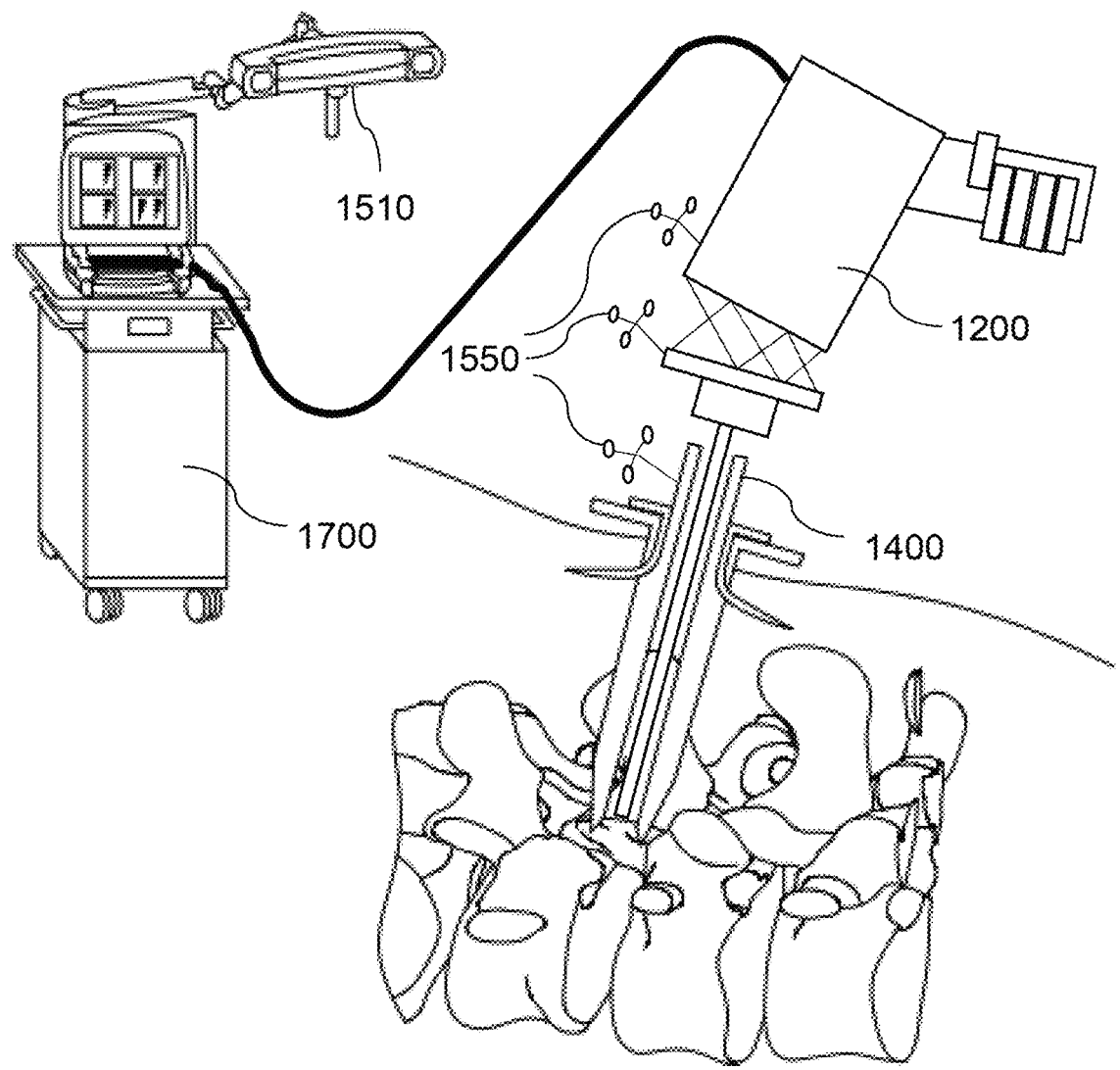
FIG. 9 is a schematic illustration of an operation state of the surgery assistive system in accordance with an embodiment of the present disclosure.

Referring to FIG. 9. The instrument 1200 may be used with a trocar 1400, especially in a minimally invasive surgery, to provide a physical portal for the tool 1250 of the instrument 1200 to reach the anatomical site of interest. In an alternative embodiment, the trocar 1400 may be removably connected to the platform 1230 of the manipulator 1210 to enable simultaneous entry of the trocar 1400 and the tool 1250 into the anatomical site.

Figure 10:
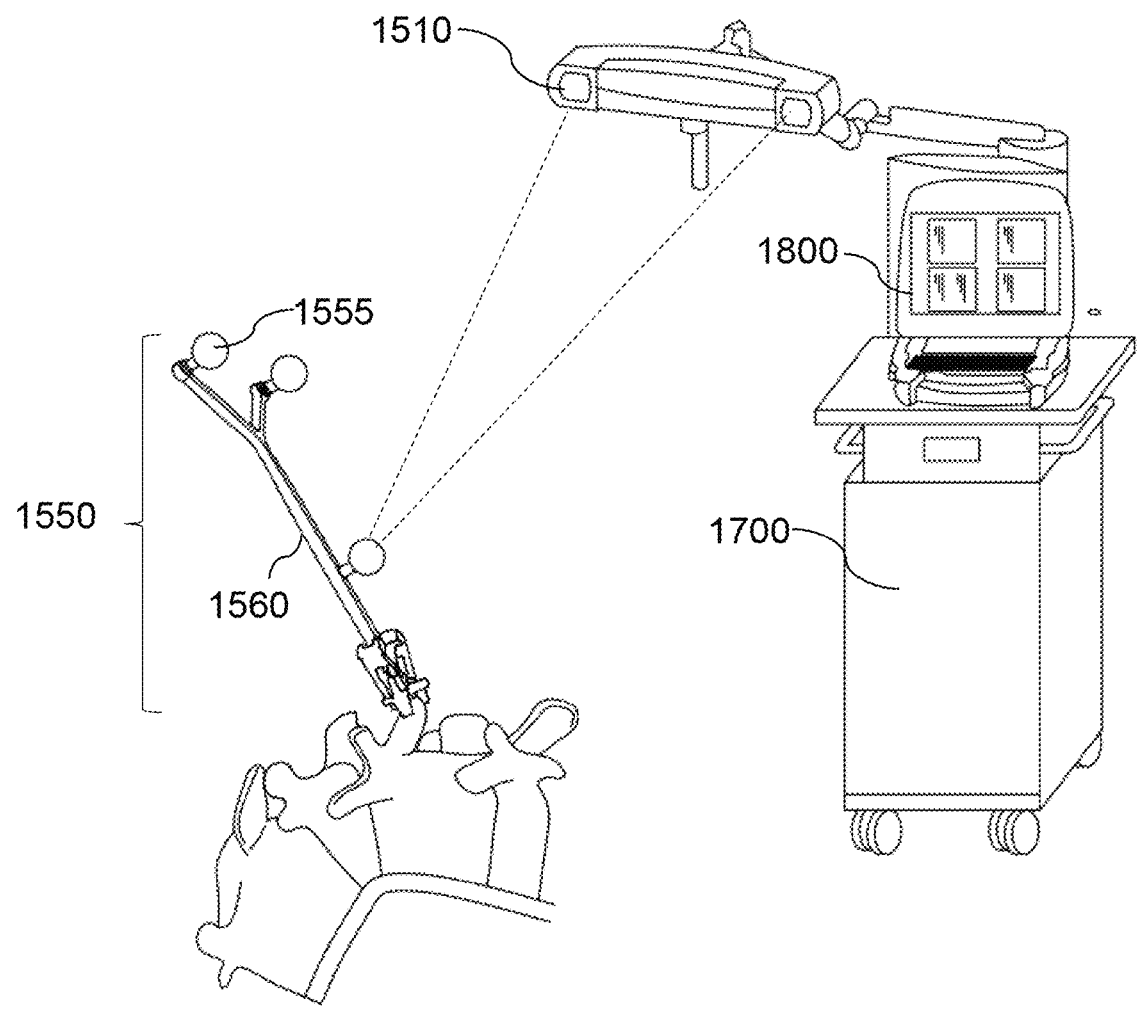
FIG. 10 is a schematic illustration of an operation state of a spatial sensor system of the surgery assistive system in accordance with an embodiment of the present disclosure.

Referring now to FIG. 10. According to an embodiment of the present disclosure, the spatial sensor system 1500 of the surgery assistive system 1000 is configured to detect and thus enable tracking of the spatial information (e.g., location and orientation) of at least one target object, and includes at least one spatial marker frame 1550 removably attached to the target object, and a spatial sensor 1510 having at least one camera for receiving signals transmitted from the spatial marker frame 1550.

As exemplified in FIG. 9 and FIG. 10, the target object may be the instrument 1200, the trocar 1400, or a selected anatomical site. In the embodiment, the spatial marker frame 1550 includes a plurality of markers 1555 for emitting electromagnetic signals, sound wave, heat, or other perceivable signals, and an adaptor 1560 removably attached to the target object for holding the markers 1555 so that the target object becomes trackable by the spatial sensor 1510. In another embodiment, the spatial sensor system 1500 may further include a signal generator (not shown in figure) disposed on the spatial sensor 1510 or at a predefined location. Consequently, signal transmission by the markers 1555 may be active or passive; in other words, the signals emitted by the markers 1555 may be generated by the marker spheres, or the markers 1555 may be covered with reflective material so that signals generated by the signal generator are reflected by the markers 1555 to the spatial sensor 1510.

In the embodiment, the signal received by the spatial sensor 1510 is transmitted to the computer system 1700 and transformed into a coordinate system of the detected space and spatial information of the target object by triangulation or other transformation algorithm. Further, the markers 1555 of the spatial marker frame 1550 may be arranged on the adaptor 1560 in a specific pattern, as exemplified in FIG. 10, thus allowing the computer system 1770 to generate orientation information of the target object accordingly. The computer system 1700 may generate control signals according to the spatial and orientation information to control movement or alter kinematic state of the manipulator 1210 of the instrument 1200 or generate instructions to be shown on the user interface 1800 to prompt the user to move the instrument 1200 to a designated location or orientation.

The position of the tip of the tool 1250 may also be trackable by the spatial sensor system 1500. Specifically, given that the distance between the tool tip and the platform 1230 of the manipulator 1210 is known, the user may dispose a spatial marker frame 1550 at the platform 1230 and allows the spatial sensor system 1500 to track the position and orientation of the platform 1230, therefore obtaining the position of the tip of the tool 1250.

According to an embodiment of the present disclosure, the computer system 1700 of the surgery assistive system 1000 includes a processor and a storage unit. The processor may be a general purpose processor, an application-specific instruction set processor or an application-specific integrated circuits that performs operations on a data source, such as the storage unit or other data stream. For example, the processor is an ARM based processor or an 8086$x$ processor. In some embodiments, the processor further includes a plurality of digital or analog input/output, and may be a real-time operating system (RTOS) processor. The storage unit may store digital data assigned by the processor for immediate use in the computer system. The storage unit may be volatile, such as flash memory, read-only memory (ROM), programmable read-only memory (PROM), and erasable programmable read-only memory (EPROM), or non-volatile, such as dynamic random access memory (DRAM) and static random access memory (SRAM).

According to an embodiment, the user interface 1800 includes at least one output device for presenting information to the user and at least one input device. The information presented by the user interface 1800 may include, but is not limited to, surgical plans, two-dimensional (2D) or 3D reconstruction images, 2D or 3D drilling status (e.g., position, angle, depth or bending of the tool), compensation range of the tool, user guidance, warning area, notification of tool deviation from the surgical plan and notification of force sustainability limit of the tool. The output device may be a display, a light indicator or other visual means; alternatively; the output device may also be, or further include, a speech synthesizer or other audio means. The input device is capable of transducing commands entered by the user into electrical signals, and may be a pedal, a keyboard, a mouse, a touch panel, a voice recognition interface, or a gesture recognition interface.

Figure 11:
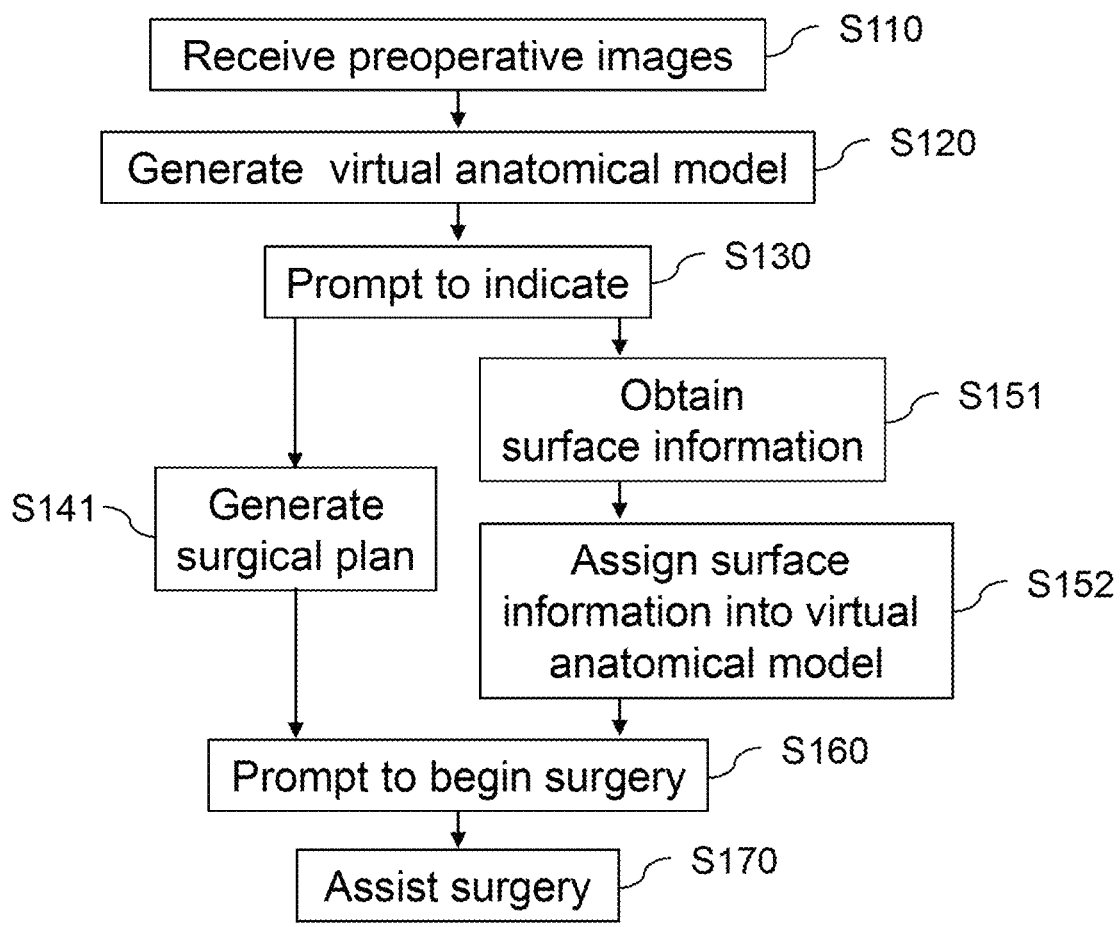
FIG. 11 is a flow diagram of an operation method of the surgery assistive system in accordance with an embodiment of the present disclosure.

Referring to FIG. 11. According to an embodiment of the present disclosure, a method of performing a computer-assisted surgery by the surgery assistive system 1000 includes the steps of: (S110) receiving a plurality of medical images from the medical imager 1910; (S120) generating a three-dimensional virtual anatomical model according to the medical images; (S130) prompting the user to indicate location(s) of interest on the virtual anatomical model; (S141) generating a surgical plan according to the virtual anatomical model, the indicated location(s), and physiological and/or pathological information obtained from the medical images; (S160) prompting the user to begin surgery according to the surgical plan; and (S170) assisting the user during the surgery.

Figure 12:
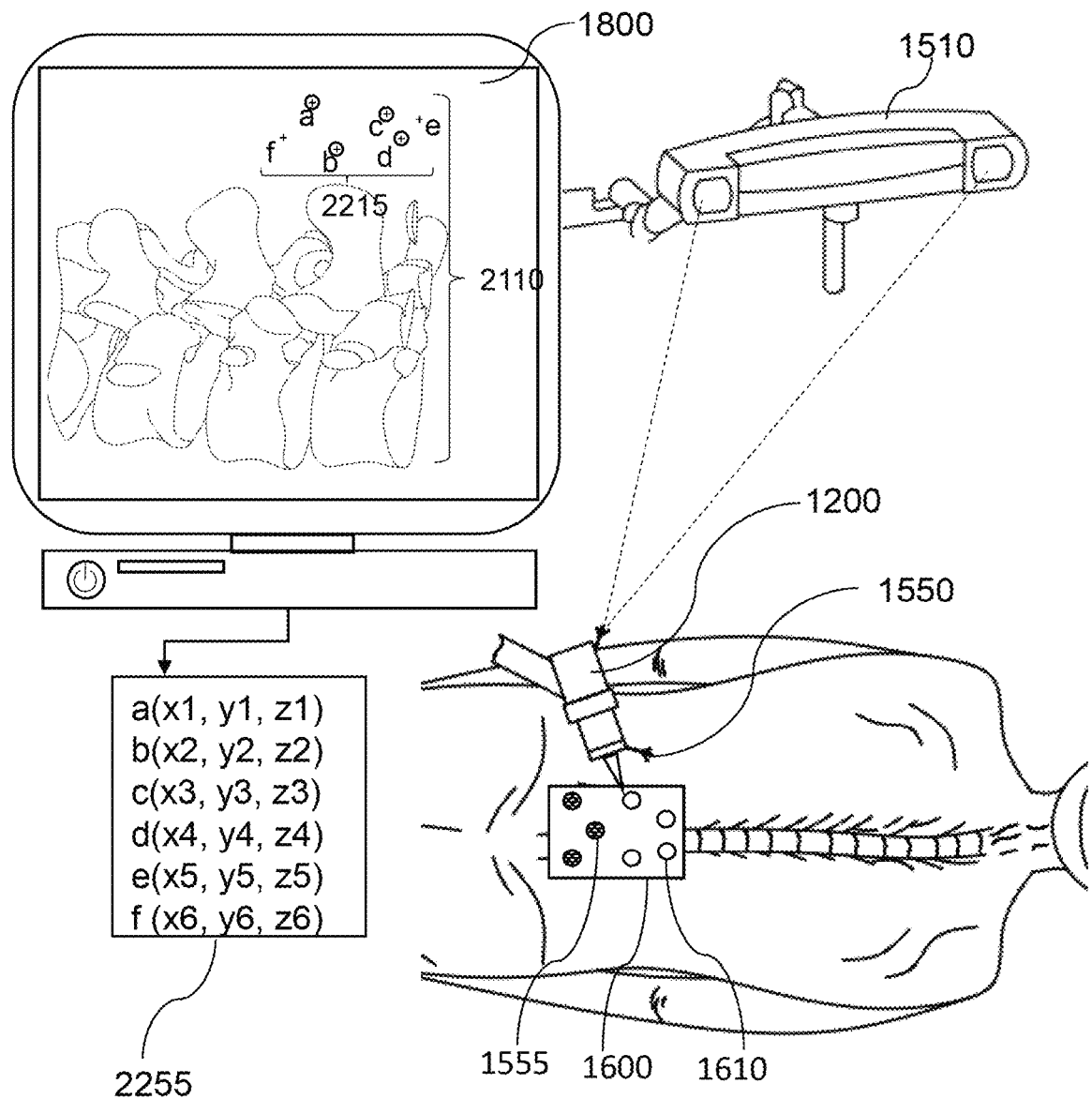
FIG. 12 is a schematic illustration of a snapshot of a preoperative registration process of the surgery assistive system in accordance with an embodiment of the present disclosure.

In Step S110, the medical imager 1910 may be a computed tomography (CT) scanner, a magnetic resonance imaging (MRI) scanner, or other commonly used medical imaging equipment that is capable of acquiring consecutive cross-sectional images of the scanned subject. In a preferred embodiment, a marker patch 1600, as illustrated in FIG. 12, is attached to the subject near the intended surgical site when the medical images are taken, to facilitate positioning of the surgical environment. Specifically, the marker patch 1600 may include at least one marker 1555 detectable by the spatial sensor 1510 of the spatial sensor system and a plurality of fiducial markers 1610 that cause markings on images taken by the medical imager 1910. The fiducial markers 1610 may be made of lead, iron, calcium, or other radiopaque metals. Therefore, as exemplified in FIG. 12, in the case where the marker patch 1600 is attached to the subject when taking the medical images, the resulting virtual anatomical model 2110 would include a plurality of radiopaque spots corresponding to the fiducial marker 1610.

In another embodiment, the markers 1555 on the marker patch 1600 may be disposed concentrically with the fiducial markers 1610 so as to avoid signal inconsistency caused by varying surface contour of the subject. Alternatively, the marker patch 1600 may be disposed with materials that are both optically readable by the spatial sensor system 1510 and radiopaque to the medical imager 1910 to ensure higher consistency between the acquired signals.

Referring again to FIG. 11. In Step S130, the user is prompted to indicate one or more locations of interest on the virtual anatomical model 2110 via the user interface 1800. The location of interest may include an intended surgical site or a specific anatomical landmark or surface feature. The user may also be allowed to label or define specific landmarks or surface features on the virtual anatomical model. In Step S141, the surgical plan generated by the method may include operative details, such as location and angle of tool entry and depth and path for the planned drilling, suggested type of tool, and suggested type of screw.

In Step 160, after the surgical plan is generated, the computer system 1700 prompts the user to begin surgery according to the surgical plan. The user may be allowed to adjust or edit the surgical plan before the surgery begins. In Step S170, the surgery assistive system 1000 assists the user during the planned surgery by adjusting the kinematic state of the manipulator 1210 according to the spatial information of the tool as detected by the spatial sensor system, and informs the user via the user interface 1800. Further, in some embodiments, medical images may also be taken during the surgery to monitor the location, angle, and depth of the drilled path so as to ensure compliance with the surgical plan and to help determine the necessity to redefine a new surgical plan or to recalibrate the instrument.

After the user selects a location of his/her interest in the virtual anatomical model in Step S130 the method according to the embodiment may further include the steps of: (S151) obtaining surface information of a plurality of sampling points on the anatomical site of the subject; and (S152) assigning the surface information into the virtual anatomical model, thereby registering the virtual anatomical model into the coordinate system established by referencing the spatial information obtained by the spatial sensor system 1500.

Figure 13:
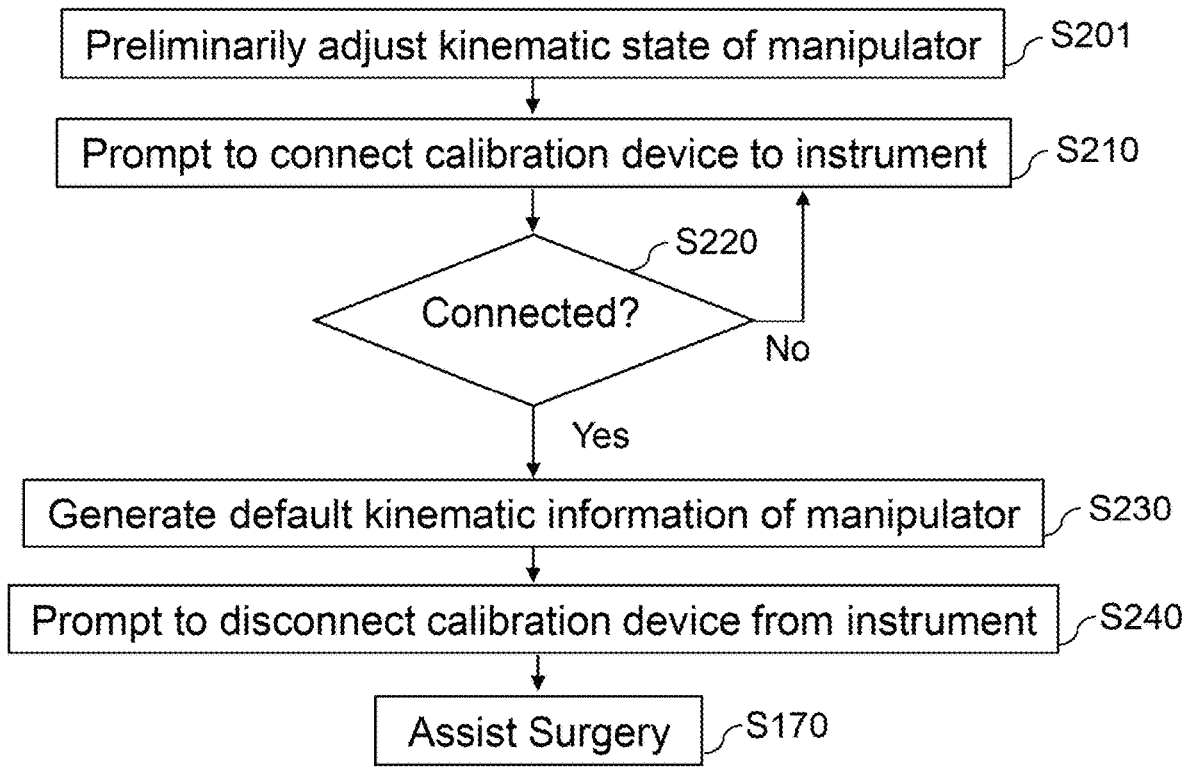
FIG. 13 is a flow diagram of the steps of calibrating the hand-held instrument of the surgery assistive system in accordance with an embodiment of the present disclosure.

Referring to FIG. 13. An embodiment of the present disclosure provides a calibration method performed by the computer system 1700 for calibrating the kinematic state of the manipulator 1210 of the instrument 1200 and defining a default kinematic state of the manipulator 1210. The calibration method may be performed preoperatively after the user indicates the location(s) of interest in step S130 or before the user begins surgery in step S160, or performed intraoperatively when the user feels the need to recalibrate the manipulator 1210. The calibration method includes the steps of: (S210) prompting the user to connect the calibration device 1300 to the instrument 1200 by passing the stabilization members 1330, 1350 through the rigid body 1310 of the calibration device 1300 and attaching the stabilization members 1330, 1350 to the base-side reference 1339 and platform-side reference 1359 on the instrument 1200, respectively; (S220) determining if the calibration device 1300 is properly connected to the instrument 1200; and (S230) generating the default kinematic information of the manipulator 1210 if the calibration device 1300 is properly connected to the instrument 1200.

In the embodiment, the manipulator 1210 may be preliminarily adjusted to a kinematic state similar to the default kinematic state to facilitate connection of the calibration device 1300 to the instrument 1200 in step S210. In other words, prior to step S210, the calibration method may further include a step of: (S201) adjusting the manipulator 1210 so that the kinematic state thereof is close to the default kinematic state. In some embodiments, the manipulator 1210 may also be adjusted manually by the user; in other words, prior to step S210, the calibration method may further include a step of: prompting the user to adjust the manipulator 1210 so that the kinematic state thereof is close to the default kinematic state. Furthermore, Step S201 may also be performed prior to shutdown of the surgery assistive system 1000 or before placing the instrument 1200 onto the instrument holder 1390.

In step S220 of the embodiment, proper connection between the calibration device 1300 and the instrument 1200 is determined according to receipt of a confirmation signal entered by the user via the user interface 1800 and/or sent from the connection sensing mechanism of the calibration device 1300. If the calibration device 1300 and instrument 1200 are not properly connected, the computer system 1700 repeats steps S210 and S220 until proper connection is detected.

After the calibration device 1300 is properly connected to the instrument 1200 (i.e., the kinematic state of the manipulator is defaulted by the calibration device 1300) in step S220, the computer system 1700 detects the kinematic state of the manipulator 1210 and generates default kinematic information that may include, but is not limited to, position and orientation of the platform 1230, rotational angles of the joints 1245*a-b*, 1246, 1247, and lengths of the actuators 1240. In some embodiments, the computer system 1700 may further utilize the default kinematic information to calibrate the spatial sensor system 1500 and/or the manipulator sensors of the instrument 1200 to ensure positional accuracy of the surgery assistive system 1000.

After the default kinematic information is generated, the calibration method may optionally include a step of: (S240) prompting the user to disconnect the calibration device 1300 from the instrument 1200. After the calibration device 1300 is disconnected from the instrument 1200, the computer system 1700 assists a planned surgery in Step S170 by generating control signals for adjusting the rotational angles of the joints 1245*a-b*, 1246, 1247 and/or the lengths of the actuators 1240 of the instrument 1200, therefore robotically controlling the kinematic state of the manipulator 1210 during the surgery.

To ensure compliance and accuracy of the planned surgery, the computer system may also track the position of the tip of the tool 1250 during the surgery by the spatial sensor system 1500. For example, given that the distance between the tool tip and the platform 1230 of the manipulator 1210 is a known constant, the user may attach the spatial marker frame 1550 on the platform 1230 prior to calibrating the instrument 1200, so as to allow the spatial sensor system 1500 to monitor the position and orientation of the platform 1230 during calibration and the surgery, thereby enabling the computer system 1700 to keep track of the position of the tip of the tool 1250 during the surgery.

Similarly, the position of the tool tip may also be tracked according to signals from sensors on the instrument 1200. For example, given that the distance between the tool tip and the platform 1230 of the manipulator 1210 is a known constant, the computer system 1700 may determine the position and orientation of the platform 1230 according to the changes in length of the actuators and/or rotational angles of the joints as detected by the manipulator sensors (e.g., the displacement sensors and/or angle sensors) on the instrument 1200 after calibration, thereby keeping track of the position of the tip of the tool 1250 during the surgery.

In other embodiments, the position of the tool tip may be tracked according to control signals generated by the computer system 1700 for adjusting the kinematic state of the manipulator. For example, given that the distance between the tool tip and the platform 1230 of the manipulator 1210 is a known constant, the computer system 1700 may utilize the default kinematic information as a calculation basis to determine the position and orientation of the platform 1230 according to control signals for adjusting the length of the actuators and/or rotational angles of the joints generated after the kinematic state of the manipulator 1210 is defaulted, thereby keeping track of the position of the tip of the tool 1250 during the surgery.

In sum, the various embodiments of the present disclosure provide an easy-to-operate calibration device for calibrating the kinematic state of the robotically controlled manipulator of computer assisted surgical instruments and for defining the default kinematic state of the manipulator so as to enable the computer system to track the tip of the surgical tool when the user is operating the instrument. The calibration device and method effectively improve the accuracy and precision of computer-assisted surgeries.

Numerous characteristics, advantages, and embodiments of the disclosure have been described in detail in the foregoing description with reference to the accompanying drawings. However, the above description and drawings are illustrative only. The disclosure is not limited to the illustrated embodiments, and all embodiments of the disclosure need not necessarily achieve all of the advantages or purpose, or possess all characteristics, identified herein. Various changes and modifications may be effected by one skilled in the art without departing from the scope or spirit of the disclosure. Although example materials and dimensions have been provided, the disclosure is not limited to such materials or dimensions unless specifically required by the language of a claim. The elements and uses of the above-described embodiments can be rearranged and combined in manners other than specifically described above, with any and all permutations within the scope of the disclosure.

What is claimed is:

1. A calibration device for a computer-assisted surgical instrument, comprising:
    a rigid body;
    a plurality of stabilization members; and
    a plurality of references structurally or mechanically complementary to the stabilization members and disposed on opposite sides of a manipulator of the instrument,
    wherein kinematic state of the manipulator is defaulted when the calibration device is connected to the instrument by the stabilization members passing through the rigid body and removably attaching to the references.

2. The calibration device according to claim 1, further comprising a connection sensing mechanism for detecting a state of connection between the calibration device and the instrument, wherein the connection sensing mechanism comprises at least one transmitter-receiver pair or one marker-reader pair disposed on the calibration device and the instrument respectively.

3. The calibration device according to claim 1, wherein a spatial sensor system associated with the instrument is calibrated when the calibration device is connected to the instrument.

4. The calibration device according to claim 1, wherein manipulator sensors of the instrument is calibrated when the calibration device is connected to the instrument.

5. The calibration device according to claim 1, wherein default kinematic information generated from the defaulted kinematic state of the manipulator is utilized as a calculation basis for determining a position of a tip of a tool of the instrument according to control signals generated by a computer system associated with the instrument for altering the kinematic state of the manipulator.

6. The calibration device according to claim 1, wherein the rigid body is formed as a part of an instrument holder, and the instrument holder comprises a structure that fits at least a portion of the instrument.

7. A calibration method for a computer-assisted surgical instrument and implemented by a computer system, comprising steps of:
    (S1) prompting a user to connect a calibration device to the instrument;

(S2) determining if the calibration device is properly connected to the instrument; and (S3) generating default kinematic information of a manipulator of the instrument if the calibration device is properly connected to the instrument, or returning to Step S1 if the calibration device is not properly connected to the instrument, wherein the calibration device comprises a rigid body, a plurality of stabilization members, and a plurality of references structurally or mechanically complementary to the stabilization members and disposed on opposite sides of a manipulator of the instrument, and kinematic state of the manipulator is defaulted when the calibration device is connected to the instrument by the stabilization members passing through the rigid body and removably attaching to the references.

8. The calibration method according to claim 7, further comprising a step of: adjusting the manipulator so that the kinematic state of the manipulator is close to the defaulted kinematic state.

9. The calibration method according to claim 7, further comprising a step of: prompting the user to adjust the manipulator so that the kinematic state of the manipulator is close to the defaulted kinematic state.

10. The calibration method according to claim 7, wherein connection between the calibration device and the instrument is determined according to receipt of a confirmation signal entered by the user.

11. The calibration method according to claim 7, wherein connection between the calibration device and the instrument is determined according to receipt of a confirmation signal sent from a connection sensing mechanism.

12. The calibration method according to claim 7, wherein the step S3 further comprises a step of: calibrating a spatial sensor system associated with the instrument according to the default kinematic information.

13. The calibration method according to claim 7, wherein the step S3 further comprises a step of: calibrating manipulator sensors of the instrument according to the default kinematic information.

14. The calibration method according to claim 8, wherein the default kinematic information is utilized as a calculation basis for determining a position of a tip of a tool of the instrument according to control signals generated by the computer system for altering the kinematic state of the manipulator.

* * * * *